United States Patent
Colombo et al.

(10) Patent No.: US 8,545,883 B2
(45) Date of Patent: Oct. 1, 2013

(54) MODULAR SYSTEMS FOR THE CONTROLLED RELEASE OF A SUBSTANCE WITH SPACE AND TIME CONTROL

(75) Inventors: Paolo Colombo, Parma (IT); Ruggero Bettini, Torrile (IT); Patrizia Santi, Salsomaggiroe Terme (IT); Pier Luigi Catellani, Reggio Emilia (IT)

(73) Assignee: Universita' Degli Studi di Parma (IT)

( * ) Notice: Subject to any disclaimer, the term of this patent is extended or adjusted under 35 U.S.C. 154(b) by 0 days.

(21) Appl. No.: 13/410,560

(22) Filed: Mar. 2, 2012

(65) Prior Publication Data

US 2012/0183618 A1 Jul. 19, 2012

Related U.S. Application Data (63) Continuation of application No. 10/496,327, filed as application No. PCT/EP02/12988 on Nov. 20, 2002, now abandoned.

(30) Foreign Application Priority Data

Nov. 23, 2001 (IT) .............................. MI2001A2481

(51) Int. Cl.
*A61K 9/20* (2006.01)

(52) U.S. Cl.
USPC ............................ 424/464; 424/465; 424/468

(58) Field of Classification Search
None
See application file for complete search history.

(56) References Cited

U.S. PATENT DOCUMENTS

| | | | |
|---|---|---|---|
| 4,681,755 | A | 7/1987 | Colombo et al. |
| 4,839,177 | A | 6/1989 | Colombo et al. |
| 5,422,123 | A | 6/1995 | Conte et al. |
| 5,534,263 | A | 7/1996 | Wong et al. |
| 5,549,913 | A | 8/1996 | Colombo et al. |
| 6,139,865 | A | 10/2000 | Friend et al. |
| 6,303,144 | B1 | 10/2001 | Omura |
| 6,342,248 | B1 | 1/2002 | Miyabe et al. |
| 7,163,693 | B1 * | 1/2007 | Clarke et al. .................. 424/451 |

FOREIGN PATENT DOCUMENTS

EP 1 053 752 11/2000

OTHER PUBLICATIONS

International Search Report of PCT/EP02/12988, Jul. 3, 2003.
Losi et al., "Assemblage of Novel Release Modules for the Development of Adaptable Drug Delivery Systems," Journal of Controlled Release 111 (2006) pp. 212-218.

* cited by examiner

*Primary Examiner* — Hasan Ahmed
(74) *Attorney, Agent, or Firm* — Snell & Wilmer LLP (57) ABSTRACT

An innovative pharmaceutical form for controlled drug release relates to systems obtained by the assembly of individual release modules, of which the capacity to release the drug in time and in space depends on the way in which the modules have been assembled. The modular structure offers high reproducibility of manufacture and flexibility of release.

4 Claims, 5 Drawing Sheets

MODULAR SYSTEMS FOR THE CONTROLLED RELEASE OF A SUBSTANCE WITH SPACE AND TIME CONTROL

CROSS-REFERENCE TO RELATED APPLICATIONS

This is a continuation of U.S. patent application Ser. No. 10/496,327, filed on May 21, 2004, which is a National Stage Application under 35 USC 365 of PCT/EP02/12988 filed on Nov. 20, 2002, which claims priority from Italian Application No. MI2001A002481, filed on Nov. 23, 2001.

BACKGROUND OF THE INVENTION

1. Field of the Invention

The present invention concerns an innovative pharmaceutical form for controlled drug release. In particular, it refers to systems obtained by the assembly of individual release modules, of which the capacity to release the drug in time and in space depends on the way in which the modules have been assembled. The modular structure offers high reproducibility of manufacture and flexibility of release.

2. The Prior Art

The pharmaceutical industry views with great interest the new forms of administration, which are able to release the drug in a pre-programmed way. This technology is known as controlled drug release and it has provided numerous innovative products for the industry and the market. Despite the solutions proposed for the various problems of administration, the variety of the existing drugs and their different requirements continuously create the need for new forms of administration. It is therefore of great interest to be able to find a drug release system that can be adapted to different active principles, changing its characteristics by simple modifications in manufacture.

The number of drugs that have to overcome important problems of administration in order to become products is increasing constantly. It is reasonable to imagine that the near future of pharmacological therapy belongs to the drugs of biotechnological origin which, on account of their chemical structure, present important problems of administration. Nor must one forget the economic and medical value linked to the revaluation of the old molecules, which in innovative forms of administration often find new therapeutic applications. Lastly it is now a common practice to propose the new drugs in the opportune release package, delivering the same through the most suitable pharmaceutical form.

As a result of this scenario, there are various problems to be dealt with concerning drug release control in time and in space. A high number of formula would therefore be necessary, in particular for products intended for administration by mouth, which are the majority of the forms of dosing used in pharmacotherapy, since they are well accepted by patients.

Many of these oral pharmaceutical forms with controlled release have however demonstrated low bioavailability in studies in vivo. This has often been attributed to an unsuitable release speed, to the incomplete liberation of the active principle by the form itself, or to a too short period of permanence in the gastroenteric tract in which absorption takes place.

The patent literature is full of inventions which attempt to solve these problems in an innovative manner.

However, a characteristic shared by all these solutions of the prior art is that a determined drug release curve is obtained with a specific therapeutic formula characterized by a weighted quantity of excipients which are mixed with (or added to) the active principle in such a way as to influence its release. Consequently a modification, even only a marginal one, of the release characteristics generally requires reformulation of the product. For example, in the ambit of coated tablets, a modification of the thickness of the outer layer is necessary, or a modification of the layer's composition, if the speed of release is to be modified. Consequently, the formulae known in the prior art do not allow an adaptation of their release curve to certain requirements without the simultaneous modification of their composition. This general principle also applies in cases where the modification of the release characteristic does not occur by modifying the excipients contained in the formula, but, instead, by choosing determined polymorphs or suitable granule sizes of the active principle.

These products generally come up against a precise problem of controlled release which is overcome with specific means for the environment in which release must occur. For example, in the documentation collected according to the International Patent Classification (IPC), in particular in the groups PCT A61K 9/00, 9/20, it is possible to find quoted numerous patents dedicated to the problem of release with space control, by means of gastro-retentive formulae.

This case deals with the necessity of having a release system, for oral drug administration, that is able to delay the gastrointestinal transit, for example by prolonging the time of permanence in the stomach. To achieve the aim of delayed transit in the digestive tract, various technological solutions have been proposed.

For example, the adhesive properties of certain polymers have been used in order to interact with the gastric and intestinal epithelium. This has allowed the construction of so-called bioadhesive systems. However, these involve certain problems, due in particular to the too localized release of the drug, with possible irritations of the mucosa.

Another solution has concentrated on the planning of systems that are able to float on the gastric content, remaining longer in the stomach. Systems of this type have been formulated with polymers that are able to swell, forming a stable gel in contact with the gastric fluid. The drug is released from these systems by diffusion through the barrier of gelled polymer. These systems therefore present an overlapping between the release of the drug and the mechanism which determines floating.

Other solutions have led to "double layer" systems, in which one layer, containing a hydrophilic polymer and an effervescent mixture, is intended to give floatability to the system, while the other layer is composed of the active principle incorporated in a hydrophilic matrix to prolong its release. This solution, instead, presents the limitation that the floating layer is activated slowly and develops a weak buoyancy. Two objects therefore do not appear to have been solved in the development of these floating systems: the first is the possibility of lifting a high quantity of substance, the second is the object of making the time of immersion necessary to obtain floating as short as possible.

The control of gastrointestinal transit is however only part of the characteristics which a versatile and innovative controlled drug release system ought to possess. In fact most of the systems are made to control the drug release speed, irrespective of the area in which it occurs. In this case too, the patent literature is rich in examples. Among these, one example is illustrated in U.S. Pat. No. 5,534,263.

So, from what has been seen above, there is still a necessity for systems which, my means of simple and reproducible manufacture, allow a variation of drug release in different areas of the gastroenteric tract, with easily modifiable kinetics. Preferably, these kinetics should be modifiable without varying the composition of the systems. There is also the necessity to have a system that is able to satisfy the requirements of release in a certain area of the gastrointestinal tract, controlling the kinetics with which said release occurs, so as to have a constant or pulsating release, adapted to the type of drug carried and to the therapy that is to be provided.

It is therefore an aim of the present invention to overcome the disadvantages of the prior art and to provide systems for the controlled release of an active principle which are more versatile than the currently known forms of administration and which allow the modification not only of the site but also of the kinetics of release of the active principle in the gastrointestinal tract without requiring important contrivances during their manufacture. Preferably, these systems for the controlled release of an active principle should be adaptable to the site and to the release kinetics desired in the gastrointestinal tract without any modification of their composition.

SUMMARY OF THE INVENTION

These and other aims that will appear more clearly below are achieved by a module for controlled drug release in the gastrointestinal tract, composed of a matrix of biocompatible polymers comprising optionally an active principle and excipients generally recognized as safe, said module being of cylindrical or polyhedric shape characterized in that it has in the case of cylindrical shape, at least one concave cylinder base;

in the case of polyhedric shape, at least one concave face of the polyhedron.

A preferred embodiment of the present invention is composed of a module for controlled drug release in the gastrointestinal tract, composed of a matrix of biocompatible polymers comprising optionally an active principle and excipients generally recognized as safe, said module being of cylindrical or polyhedric shape characterized in that it has in the case of cylindrical shape, one of the two bases of the cylinder concave and the other convex;

in the case of polyhedric shape, at least one of the faces of the polyhedron concave and at least one other of the faces of the polyhedron convex.

According to a preferred but not exclusive embodiment of the present invention, at least two modules assembled as describe above are provided, or at least one module as described above assembled with a cylindrical/polyhedric element with flat bases. While the modules according to the invention—when administered in non assembled form—must always comprise at least one active principle, instead, in the assemblies according to the invention, it is also possible to incorporate further modules according to the invention which are however without active principle (so-called "auxiliary" modules). This is possible in all those cases in which the assembly already comprises, at least one module according to the invention containing active principle or at least one cylindrical/polyhedric element with a flat base, also containing active principle. Hence, on account of its utility in the construction of an assembly according to the invention, also the "auxiliary" module according to the invention is to be understood as a module "for controlled drug release in the gastrointestinal tract".

Returning now to the particular geometry of the modules according to the invention, according to a preferred embodiment, the concave base/face of a first cylindrical/polyhedric module according to the present invention is configured in such a way as to be able to accommodate a corresponding convex base/face of a second module according to the invention to give an assembly between the two modules. Preferably, the joint thus obtained between the two modules is not visible from the outside of the resulting assembly. Preferably, this joint is also sufficiently strong from a mechanical point of view to hold the two modules together in conditions of use. Moreover, according to the same or according to a further preferred embodiment of the invention, the concave base/face of a first cylindrical/polyhedric module according to the present invention is configured in such a way as to allow to obtain an assembly with an internal (that is totally isolated) cavity to be obtained if said concave base/face is placed adjacent to a planar base/face of a second module according to the invention (or of a cylindrical or polyhedric-element), or if said concave base/face of said first module is placed adjacent to a concave base/face of the second module according to the invention. The internal cavity produced in the resulting assembly (obtained then by subsequent gluing/welding of the adjacent bases/faces)—in the case of concave bases/faces placed adjacent to each other—is larger than the one obtained in the case of a concave face/base placed adjacent to a flat one.

According to a further aspect of the present invention, a method is provided for the production of a module according to the present invention comprising the following steps:

the provision of a biocompatible polymer in a granule size suitable for compacting by pressure, and, optionally, the provision of an active principle and of optional excipients generally recognized as safe, the mixing of the components provided, the compression of the mixture of components or of only the granules of biocompatible polymer in a tablet press provided with at least one convex punch for giving a concave base/face to the compressed module thus obtained.

BRIEF DESCRIPTION OF THE DRAWINGS

The invention described and claimed in the present patent application is further illustrated in the enclosed Figures, which refer to a preferred but not exclusive embodiment of the invention and in which:

FIG. 7 is the graphic representation of the comparison, according to examples 2 and 3, between the release of the drug acyclovir (in percentage, shown on the Y axis; in time (min), shown on the X axis) by four individual modules according to the invention with a cylindrical shape having one concave base and one convex base (circles) and by an assembly according to the present invention composed of four modules having one concave base and one convex base assembled in such a way that the convex faces fit into the concave ones to give a long cylinder as in FIG. 4 (rhombi) and by two assemblies according to the present invention composed in turn of two modules with a cylindrical shape having one concave base and one convex base according to the invention, assembled in such a way that the concave bases face each other reciprocally, as in FIG. 5 (squares).

Even though not explicitly represented in the FIGS. 1-7 it is however implied that, according to further preferred embodiments of the present invention, the individual modules according to the invention with a cylindrical shape may have two concave bases or one flat base and the other concave. Even though not explicitly represented in the FIGS. 1-7 it is however implied that, according to further preferred embodiments of the present invention, the individual modules, instead of being cylindrical, may also be polyhedric (for example they may form tetrahedrons, prisms or cubes), at least one of the faces of the polyhedron being concave and, optionally, at least one other of the faces of the polyhedron being convex. For example, a polyhedric module according to the present invention may be cubic and have one concave face and one convex face, or have two concave faces, or two convex faces and three concave faces, and so on.

SOME ASPECTS OF THE INVENTION

According to the invention described in the present patent application, a new kit is therefore provided for the preparation of new drug release systems having characteristics such as to satisfy various requirements of time or space control of release. These new systems are made according to a modular principle, based on a construction unit called a module (release module or "auxiliary" module). Like a brick used for building a wall, the (release or "auxiliary") module is a unitary element which has an autonomous function of its own, but which, when grouped together with other like or similar modules, it gives rise to a system which releases the drug with different kinetics, or in different tracts of the gastrointestinal apparatus, depending on how the individual modules have been assembled. For the present invention it is essential that the module (release or "auxiliary") be composed of a matrix with a cylindrical or polyhedric shape, characterized in that at least one base/face of the matrix is concave. According to a preferred embodiment of the invention, it is essential that the module (release or "auxiliary") be composed of a matrix with a cylindrical or polyhedric shape, characterized in that at least one base/face of the matrix is concave and at least one other convex. This matrix is a non disintegrating monolith, composed of a mixture of active principle (and eventually of excipients generally recognized as safe) with a biocompatible polymer which in some applications may be a hydrophilic polymer, which gels and/or swells in the presence of an aqueous solvent. The preferred technique for manufacturing the matrix is that of the compression of powders. It is important to note that the particular geometry of the bases or faces of the cylindrical or polyhedric matrix which forms the release module is already itself an element for the control of the speed of release of the drug from the same. For example, especially when the polymer is of the hydrophilic type, the two bases of the cylindrical module, of which, for example one is concave and the other convex, alter the swelling of the module and therefore the drug release kinetics. With respect to a "simply cylindrical", element, that is a cylindrical tablet with flat base with an identical composition, the geometry of the module with the bases modified according to the present invention produces with the same weight varied kinetics, since in the initial stages the swelling of the matrix does not take place isotropically.

But the point which more than any other qualifies the invention described in the present patent application is that the innovative geometric shape of the release modules allows further elements to be provided for exerting space and time control of the release from the system. In fact, according to a preferred embodiment of the present invention, by fitting the convex face of one module into the concave face of another, different release modules may easily be stacked one on another, to produce a long cylinder. Generally, such stacked modules are introduced preferably, but not necessarily, in a hard gelatine capsule to assist their administration by mouth. In the gastrointestinal tract, during the drug release phase when the optional capsule has been disintegrated, the stacked modules, depending on the biocompatible polymer material of which the matrix is made—and depending on the quality of the join obtained by the assembly of the convex faces with the respective concave faces—separate or do not separate into the individual modules.

In particular, in some conditions, for example due to the adhesive properties of the gelled hydrophilic polymers, the stacked release modules may remain stuck together, forming a so-called assembly according to the present invention and producing release kinetics different from that obtained with separate modules. However, it should be stressed that even with non-adhesive polymers, depending on the hardness of the modules and on the geometric design of the concave and convex faces, it is possible to obtain a fairly stable and lasting mechanical join so as to give assemblies according to the present invention which, during the drug release phase, also do not separate into the individual modules. Moreover, even in cases where the adhesive or mechanical properties of the polymers used are poor, to obtain an assembly according to the present invention which allows a variation of the drug release kinetics, it is always possible to reinforce the join between the modules by gluing or welding (for example thermal welding or with ultrasounds) of the individual modules so that the assembly thus obtained has the shape of a long cylinder, the component modules of which cannot come apart. This more stable assembly is obtained, for example, by placing a small quantity of solvent or of adhesive solution between one module and the other, before introducing them in the gelatine capsule.

The inventors of the present patent application have also found that, since it is possible to stack the modules differently from simply fitting a convex face into a concave one, the possibilities of release control are even greater. For example, in the case where two modules are welded together with a solvent or an adhesive solution, placing the two concave faces in contact ("joining"), a two-module system is created which has an air chamber inside it. This obtains immediate floating of the system with two welded modules when it is immersed in water. Also these two-module systems can be administered directly or after having been inserted in a rigid gelatine capsule.

In addition, since the two modules welded by the concave faces give rise to a system with a cylindrical shape (FIG. 5) which has two convex bases, it is possible to add further modules, fitting their concave bases against the two convex bases of the floating system. The result obtained is a system, still floating, which contains more drug and possesses a still different release kinetic. The inventors of the present patent application have also found that the cavity formed when gluing together two modules according to the present invention, concave face against concave face, before welding of the two modules, can be filled with a dispersion of a drug in an excipient, preferably presenting a low melting point such as semi-synthetic glycerides or cacao butter. This combination allows an assembly which carries a further dose of drug destined to be released after a certain period of time, or in a different area of the gastrointestinal tract, in the moment in which the system is then demolished.

Lastly in the case where, individual modules having a different form and composition are assembled with the modules which possess two modified faces, further drug release systems are obtained which produce different kinetics and different space-time behaviors. In particular, in the case of the assemblies according to the invention—and preferably in the case where said assemblies contain cavities (to guarantee the floating of the assembly or to carry drugs released only at the moment of demolition of the matrix)—it is also possible to use, for the construction of the assemblies, further to the release modules according to the invention as described above, at least one further module according to the invention (so-called "auxiliary" module) which is also composed of a matrix of biocompatible polymers but without a active principle. Lastly, said "auxiliary" modules according to the invention (like their respective equivalents comprising instead the active principle) can also be combined with "simply" cylindrical elements, that is with flat bases (or with "simply" polyhedric elements, that is with flat faces), also composed of a matrix of biocompatible polymers and comprising an active principle, thus obtaining further assemblies according to the present invention. It has been seen how, using the new modules of the present invention, it is possible to construct—even incorporating elements with a traditional geometry (e.g. tablets)—new assemblies with modified drug release kinetics, for example new floating assemblies.

It has also been seen how the present invention, with respect to the prior technique, allows various advantages to be obtained, for example:

the extreme ease of manufacture of the tablet to be used as the release or auxiliary module (e.g. in the case of the cylindrical module with one concave base and the other convex) with the ordinary techniques for compressing powders;

the manufacture of different drug release systems by simply combining together some of these modules having a precise composition and a particular geometry, fitting the convex face into the concave one, obtaining respective assemblies;

the possibility of constructing release systems with a very elongated cylindrical shape, favoring the assembly of the modules with an adhesive solution to give respective assemblies;

the possibility of time and space control of the release of active principle by the modules according to the invention, deriving from the modular principle and in particular from the specific way in which the modules have been assembled, without changing the composition and the geometry of the individual modules;

the obtaining of varied drug release kinetics according to the number and respective position of the modules in the release system;

the obtaining of a prolonged release in a specific site of the stomach, in the case where two modules have been joined together to create a cavity in the assembly obtained, allowing it to float;

the obtaining of a system able to provide a delayed impulse of active principle for release in the colon, in the case where the cavity between two assembled modules is filled with a preferably semi-solid mixture comprising an active principle;

the increased possibility of flexibility of release by mixing modules with a different composition or different geometry in the assemblies.

DETAILED DESCRIPTION OF THE INVENTION

Figure 1:
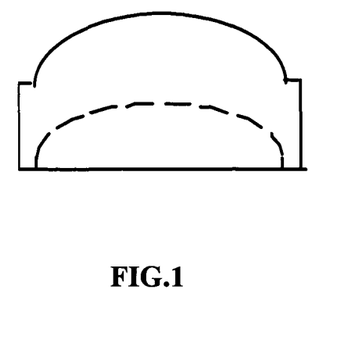
FIG. 1 is a schematic representation of a side section of an individual module according to the present invention with a cylindrical shape, having one base concave and the other base convex.
Figure 2:
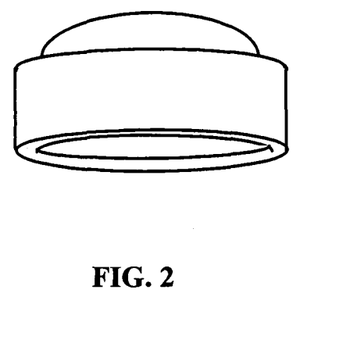
FIG. 2 is a representation of the three-dimensional side view of the same module according to the present invention.

An important aspect of the invention is the release module and its manufacture. For reasons of ease and versatility of the product, using classical techniques and ordinary compressing machines, it has been possible to produce a release module having the shape of a cylindrical polymer matrix with one concave base and the other convex (FIGS. 1 and 2). One of the reasons for this new geometry is that it favors the assembly of the release modules, to obtain a system that cannot be made directly, in which to change the kinetics according to the type of assembly.

To increase the capacity of the release modules to remain assembled together and to control drug release, a component may be introduced into the composition such as a swelling and gelling hydrophilic polymer, generally, but not necessarily, with a high molecular weight. In this case the composition of the module is that of a hydrophilic matrix. These types of polymer are easily available on the market, for example, as illustration without limitation, hydroxypropylmethylcellulose, known by the commercial name METHOCEL® hydroxypropyl methylcellulose in grades K4M, K15M and K100M (Dow Chemical Company); or other polymers such as xanthan gum, pectin, carrageenans, guar gum. The quantity of these polymers used to obtain the control of the release of active principle by the release module is that commonly described in the literature, and varies preferably between 20 and 60% weight/weight referred to the total composition of the matrix which may also comprise excipients generally considered safe as well as the active principle which may be any one of the active principles contemplated by the Pharmacopoeia for oral administration. With respect to the total composition, the contribution of the active principle varies preferably between 80% and 0.0001% weight/weight.

The inventors of the present patent application have found that the assembly of the release modules making up the finished system ("assembly") can be easily obtained, including in the release module a polymer with strong adhesive properties such as sodium carboxymethylcellulose, carboxypolymethylene, hydroxypropylcellulose, hydroxypropylmethylcellulose, methylcellulose, polymethacrylate or others. In this way, the release system can be obtained by inserting the release modules in a hard gelatine capsule, in the sequence concave face against convex face, so that they are in close contact with each other in forming the assembly. When the gelatine capsule is immersed in the gastric fluid at 37° C., the gelatine component softens and dissolves, creating, around the pile of modules inserted in the capsule, a layer of sticky material which holds them together for a brief period due to the complete dissolving of the gelatine. During this period the gastric fluid also comes in contact with the modules included in the capsule. They are thus able to gel on the outside, giving rise to a sticky layer which welds them very firmly together. A cylindrical assembly is thus obtained (with one concave base and the other convex, as in FIG. 4), having the same base area as the modules of which it is composed, with a height smaller than the sum of the individual heights of the single modules. This cylinder, which possesses an unusual geometry for pharmaceutical forms, may (in the case of polymers with a low apparent density), but need not, show the capacity to float due to the intrinsic property of the modules of which it is composed. It is subject to a very slow phenomenon of swelling and dissolving, which guarantees slow drug release and self-destruction only at the end of the drug release period.

Since the individual modules are assembled to obtain various release systems, in some situations it is preferable that they are assembled in such a way as to produce an assembly in which the various individual modules are even more firmly fitted and stuck together. In this case the gluing of the modules fitted convex face into concave face (FIG. 4) is further strengthened with a solution or suspension of a biocompatible polymer such as ethylcellulose, cellulose acetate phthalate or other polymers, but also with an aqueous solution of water-soluble polymers such as high-viscosity carboxymethylcellulose. Alternatively, the welding of the modules may also be obtained by means of thermal welding or ultrasound welding.

Moreover, the inventors of the present patent application have found that, in the case where the modules are welded two by two, concave face against concave face, the resulting assembly, due to the formation of an insulated internal cavity (FIG. 5), besides presenting a varied release kinetics, shows the immediate capacity to float in water (that is even if the apparent density of the polymer matrix exceeds the density of water). This gluing is achieved: by placing in contact the concave faces of the cylindrical modules, on which a small amount of adhesive polymer solution has been applied, or by means of thermal welding or ultrasound welding.

The inventors of the present patent application have also discovered the possibility of creating a floating release system by combining cylindrical modules with one concave and one convex base (or with one concave base and the other flat, or with two concave bases), with other "simple" cylindrical elements with flat bases. The modules with a concave and a convex base according to the invention are intended to give floating capacity (and therefore so-called "auxiliary" modules can, but need not, be used, that is to say modules without active principle, that is composed of biocompatible polymers possibly mixed with excipients generally recognized as safe), whereas the cylindrical elements with flat bases are intended for drug release. This can be achieved by stacking the release element between two or more floating modules depending on its weight. In fact, by placing both flat faces of the release element in contact with a concave base of the floating module, two float chambers are created which are able to develop a total buoyancy able to render floating the new assembly thus obtained. In particular, for the functioning of the finished assembly the release element must be firmly glued to two or more floating modules. In this case the swelling of the two or more floating modules does not interfere with drug release, which takes place through the exposed surface of the release element. After the floating phase, the whole system is slowly destroyed.

In this variation, to further strengthen the floating power, the floating module may be composed of a mixture of a hydrophilic polymer and a low-density hydrophobic component (that is one that reduces the apparent density of the overall polymer matrix). By contact with the gastric fluid or with water, it rapidly reaches a stable floating situation. In order to ensure the correct functioning of the floating element, the composition of the mixture that must provide the hydrostatic thrust is essential. The inventors of the present patent application have found that the maximum result can be obtained by mixing a hydrophobic substance with a hydrophilic one, so as to give the module the lowest possible true density, together with a certain hydrophobia which favors the immediate floating of the element. As a hydrophilic substance for making the floating layer it is possible to use gellable and soluble biocompatible polymers such as: polyvinylpyrrolidone, hydroxypropylmethylcellulose, carboxymethyl cellulose, hydroxypropylcellulose, hydroxyethylcellulose, carboxypolymethylene, gums such as guar gum, xanthan gum, chitosanes, gum arabic, gum tragacanth, sodium and calcium alginates, gelatine, pectins. The hydrophobic substances that can be used may be: hydrogenated oils, cetyl, myristic and stearyl alcohol, esters of fatty acids such as glyceryl mono- or distearate.

To further increase the buoyancy of the floating module it is also possible to include a mixture of salts able to develop $CO_2$ by contact with gastric fluid: in this case the swelling of the polymer determines the formation of a gelled structure which retains the bubbles of $CO_2$ that have formed, further reducing the apparent density of the polymer matrix. The effervescent mixture may be composed of substances that produce $CO_2$ such as: calcium carbonate, calcium bicarbonate, sodium carbonate, sodium bicarbonate, potassium carbonate, potassium bicarbonate, magnesium carbonate.

Lastly, as concerns the composition of the drug release element (cylindrical or polyhedric, with flat bases/faces), as in the case of the release modules provided by the present invention, it can be given by a mixture of active principle, possible excipients generally recognized as safe and a biocompatible polymer, preferably gellable such as polyvinylpyrrolidone, hydroxypropylmethylcellulose, carboxymethyl-cellulose, sodium and calcium alginates, gum arabic, gum tragacanth.

EXAMPLE 1

The first example describes the manufacture and operation of a release module containing acyclovir. It is intended for the preparation of a system composed of a capsule containing various modules stacked in such a way as to give an assembly containing a total quantity of 400 mg of acyclovir.

The unitary formula for preparing 1250 modules, was the following:

|  | X 1 MODULE (mg) |
| --- | --- |
| Acyclovir | 100 |
| Hydroxypropylmethylcellulose | 29.5 |
| Sodium carboxymethylcellulose | 29.5 |
| NaHCO$_3$ | 12.3 |
| Talc | 6.2 |
| Mg stearate | 1.8 | a) Preparation of the Acyclovir Granulate and Mixing of the Components 125 g of acyclovir are blended with about 33 ml of a solution 8% p/v of sodium carboxymethylcellulose (Blanose 7LF). The granulate is obtained by forcing the mixture through the 500µ mesh of the net of an oscillating granulator. The granules are stove-dried with air circulating at 35° C. for about 8 hours. The remaining components of the formula are added to the acyclovir granulate and the whole is mixed in a Turbula for about 40 minutes.

b) Compression

Figure 3:
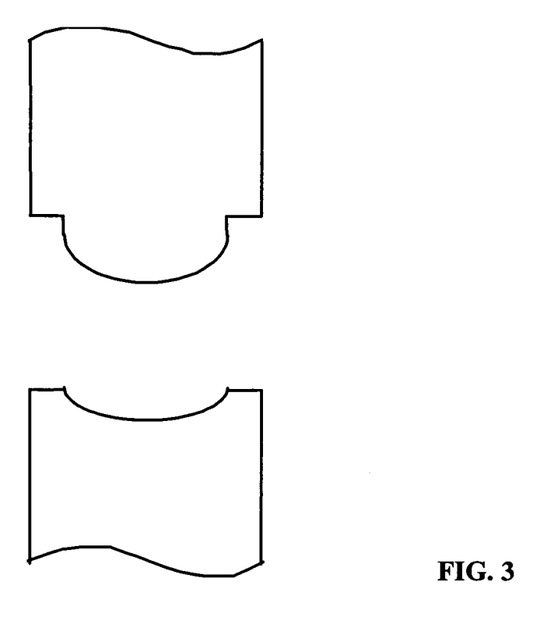
FIG. 3 is a schematic representation of a side section of the punches that may be used for making the individual modules according to the present invention (in particular the one represented in FIG. 1 or 2) by compression.

The production of the module by compression is carried out with an alternative tablet press, using special punches with diameter 7.4 mm, the drawing of which is shown in FIG. 3. The weight of each module was 191.5 mg, the diameter 7.5 mm and the mean height 5.5 mm.

c) Acyclovir Release Speed

Figure 6:
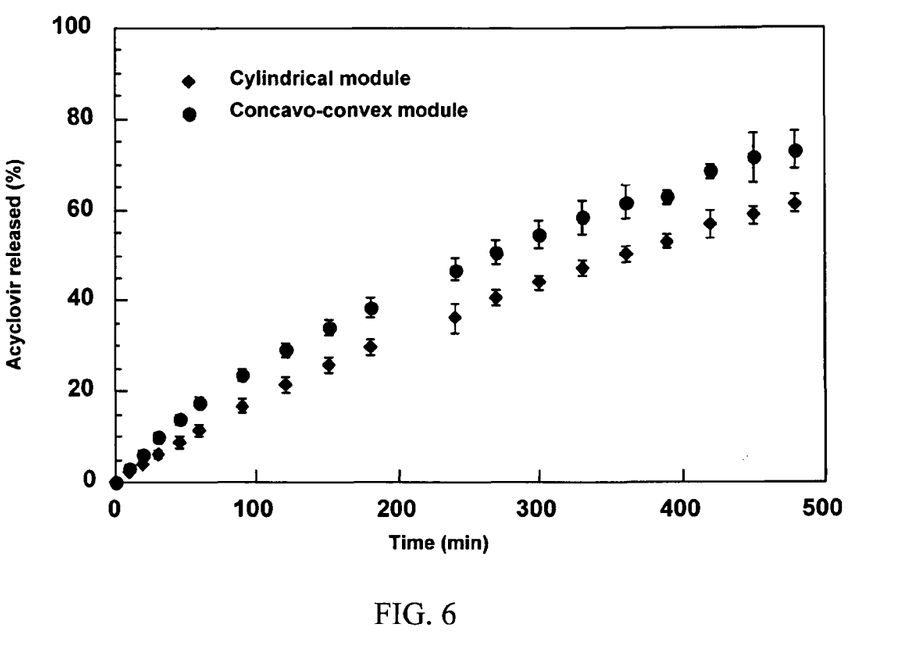
FIG. 6 is the graphic representation of the comparison, according to example 1, between the release of the drug acyclovir (in percentage, shown on the Y axis; in time (min), shown on the X axis) by an element with a cylindrical shape and flat bases (rhombi) and by an individual module with a cylindrical shape having one concave base and one convex base according to the invention (circles)

The speed at which acyclovir is released from the release module was determined at 37° C. in artificial gastric fluid with the Apparatus 2 USP 24, vane 50 rpm. The profile of the release of acyclovir from the release module is shown in FIG. 6 (circles). About 30% of the drug was released after 120 minutes and about 70% after 500 minutes. The kinetics of release from this module, which has one concave and one convex face, was faster than that of a cylindrical matrix with flat faces (FIG. 6, rhombi) having the same composition, prepared with a set of punches with diameter 7.4 mm from the same quantity of mixture. Such comparative result is shown in FIG. 6.

EXAMPLE 2

Figure 4:
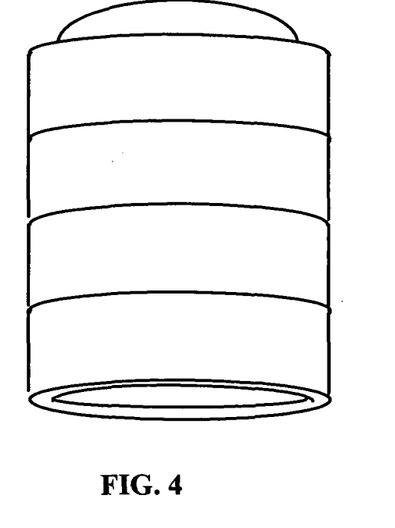
FIG. 4 is a three-dimensional side view of four individual modules according to the invention stacked in such a way that the convex base fits into the concave base to give a single assembly according to the present invention.

Four release modules, prepared according to the technique described in Example 1, were stacked one on another, with the convex faces fitted into the concave faces and stuck with a 0.5% hydroalcoholic solution (2:8) of hydroxypropylmethylcellulose phthalate (FIG. 4). The speed at which acyclovir is released from the capsule was determined at 37° C. in artificial gastric fluid with the Apparatus 2 USP 24, vane 50 rpm.

Figure 7:
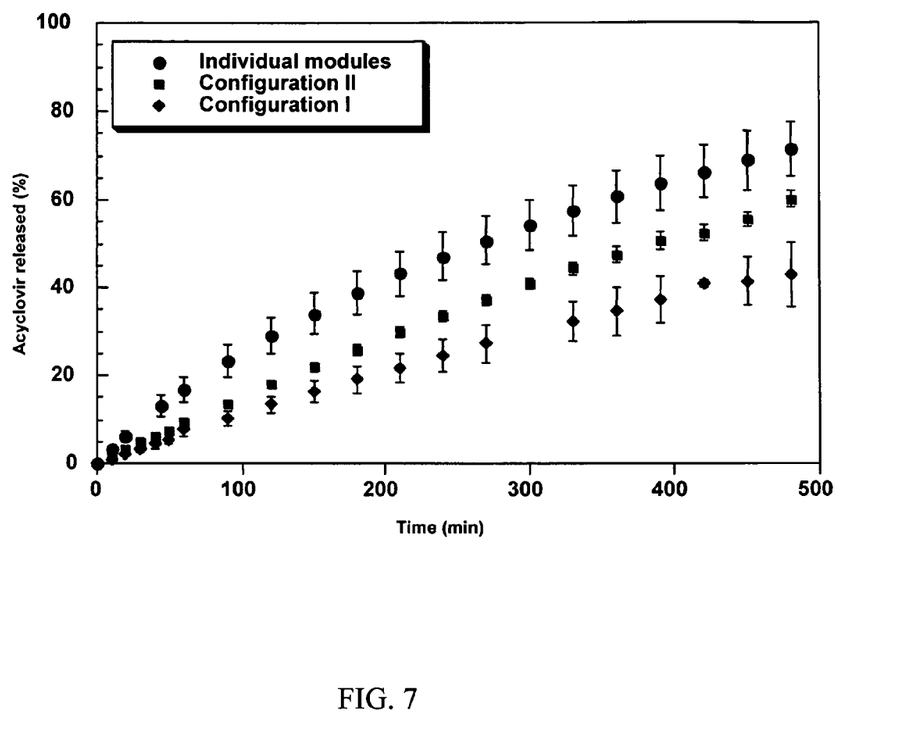

The release of acyclovir from this stacked system of four modules is shown in FIG. 7 (rhombi), in comparison with the release from the individual modules (circles). In the first 500 minutes the drug release from the four stacked and glued modules was slower and more linear than the release presented by the individual modules.

EXAMPLE 3

Figure 5:
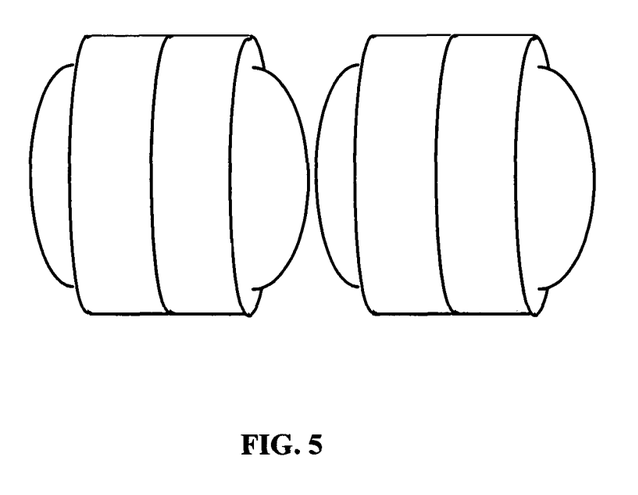
FIG. 5 is a three-dimensional side view of four individual modules according to the invention assembled with the concave bases reciprocally fitted together to give two assemblies according to the present invention.

Four release modules, prepared according to the technique described in Example 1, were glued two by two, concave face against concave face, wetting the edges of these faces with a 5% hydroalcoholic solution (2:8) p/v of hydroxypropylmethylcellulose phthalate and joining them with a light pressure, to form two assemblies of two modules (FIG. 5).

These assemblies float immediately in the dissolving fluid. The release of acyclovir from these two assemblies (FIG. 7, squares) was faster and more linear than that obtained with the four stacked and glued modules (FIG. 7, rhombi).

EXAMPLE 4

The example illustrates the preparation of a floating release system which contains the float modules separate from the release elements. For the preparation of 500 floating systems, the following substances are used in the quantities indicated:
Composition of the Release Element

| | |
|---|---|
| Aluminium hydroxide | 95 g |
| Polyvinylpyrrolidone | 4 g |
| Magnesium stearate | 1 g |

Composition of the Floating Module

| | |
|---|---|
| HydroxypropylmethylCellulose (METHOCEL ® K 100M) | 75 g |
| Hydrogenated castor oil (Cutina HR) | 15 g |
| Sodium carbonate | 5 g |
| Tartaric acid | 5 g |

Preparation of the Drug Release Element

Granulate the aluminium hydroxide and the active principle with a 1% aqueous solution of polyvinylpyrrolidone. Dry, calibrate on sieve $25_\#$. Mix with magnesium stearate and compress the mixture with a tablet press equipped with flat punches with diameter 7.4 mm.

Preparation of the Floating Module

Mix the components according to the quantities indicated in a Turbula® mixer for 15 minutes and compress the mixture with a tablet press equipped With punches with a concave and a convex face with diameter 7.4 mm.

Preparation of the Floating Release Systems

For the preparation of the finished assembly, rigid gelatine capsules are used, of the type Snap Fit™ 00, with internal diameter 8 mm and a total closed capsule height of 23.4 mm. The floating modules and the release elements are stuck together by means of a 12.5% solution of cellulose acetate phthalate in acetone, before being inserted in the capsule in the following sequence:

1 floating module
1 release element
1 floating module.

A thin film of adhesive solution is applied on the concave base of a floating module; the flat base of the release element is stuck onto this. The gluing operation is repeated, sticking a second floating module onto the second flat base of the release element.

EXAMPLE 5

For the preparation of 500 floating systems, the following substances are used in the quantities indicated:
Composition of the Release Element

| | |
|---|---|
| Aluminium hydroxide | 95 g |
| Polyvinylpyrrolidone | 4 g |
| Magnesium stearate | 1 g |

Composition of the Floating Module

| | |
|---|---|
| Crospovidone (Kollidon ® CL) | 96 g |
| Tartaric acid | 20 g |
| Sodium carbonate | 24 g |
| HydroxypropylmethylCellulose (METHOCEL ® K4M) | 54 g |
| Talc | 4 g |
| Magnesium stearate | 2 g |

Preparation of the Floating Modules

Let half the dose of Kollidon® CL absorb a quantity equal to its own weight of a 1% aqueous solution of METHOCEL® K4M hydroxypropyl methylcellulose in which the sodium carbonate has been dissolved. Let the mixture dry partly at 80° C. for 30 minutes, sieve it, complete drying and sieve it again.

Let the remaining quantity of Kollidon® CL absorb a quantity equal to its own weight of a 1% aqueous solution of METHOCEL® K4M hydroxypropyl methylcellulose in which the tartaric acid has been dissolved. Let the mixture dry partly at 80° C. for 30 minutes, sieve it, complete drying and sieve it again.

To the two mixtures, add the METHOCEL® K4M hydroxypropyl methylcellulose, the talc and the Mg stearate and mix for 20 minutes in a Turbula® mixer. Compress the mixture with a tablet press equipped with punches with a concave and a convex face with diameter 7.4 mm.

Preparation of the Release Element

Granulate the aluminium hydroxide with the active principle and with a 1% aqueous solution of polyvinylpyrrolidone. Dry, calibrate on sieve $25_\#$ and compress the mixture with a tablet press equipped with flat punches with diameter 7.4 mm.

Preparation of the Finished Systems

For the preparation of the finished system, rigid gelatine capsules are used, of the type Snap Fit™ 00, with internal diameter 8 mm and a total closed capsule height of 23.4 mm. The floating modules and the release elements are stuck together by means of a 12.5% solution of cellulose acetate phthalate in acetone, before being inserted in the capsule in the following sequence:

1 floating module
1 release element
1 floating module.

A thin film of adhesive solution is applied on the base of a release element; the concave base of the floating element is stuck onto this. The gluing operation is repeated, sticking a second floating module onto the second base of the release element.

Accordingly, while only a few embodiments of the present invention have been shown and described, it is obvious that many changes and modifications may be made thereunto without departing from the spirit and scope of the invention.

What is claimed is:

1. A module for controlled drug release in the gastrointestinal tract, consisting of a matrix of a biocompatible hydrophilic polymer, at least an active principle and excipients, said module having one of the following shapes:

a cylindrical shape, wherein the first base of the cylinder is peripherally flat and has a central dome-shaped concavity, and the second base is peripherally flat and has a central dome-shaped convexity, wherein said first base is fittable by stacking on the second base, and wherein said first base and said second base are substantially parallel, or a polyhedric shape, wherein at least one of the faces of the polyhedron is peripherally flat and has a central dome shaped concavity, and at least one other of the faces of the polyhedron is peripherally flat and has a central dome-shaped convexity, wherein said at least one face is liftable by stacking on said at least one other face, and wherein said at least one of the faces and said at least one other of the faces are substantially parallel.

2. The module according to claim 1, wherein the biocompatible polymer is selected from the group consisting of polyvinylpyrrolidone, hydroxypropylmethylcellulose, carboxymethylcellulose, hydroxypropyl-cellulose, hydroxyethylcellulose, carboxypolymethylene, guar gum, xanthan gum, chitosanes, gum arabic, carrageenan, sodium and calcium alginates, gelatine and pectins.

3. The module according to claim 1, wherein, the matrix further comprises a hydrophobic substance selected from the group consisting of hydrogenated oils, cetyl, myristic and stearyl alcohol, and esters of fatty acids.

4. The module according to claim 1, wherein the matrix further comprises an effervescent substance comprising a mixture of salts that release $CO_2$ in contact with gastrointestinal liquids.

* * * * *